United States Patent [19]

Cobb et al.

[11] Patent Number: 4,906,459
[45] Date of Patent: Mar. 6, 1990

[54] HAIR CARE COMPOSITIONS

[75] Inventors: Daniel S. Cobb, Loveland; Nancy M. Lorincz; Melissa S. Monich, both of Cincinnati, all of Ohio

[73] Assignee: The Procter & Gamble Company, Cincinnati, Ohio

[21] Appl. No.: 372,180

[22] Filed: Jun. 27, 1989

Related U.S. Application Data

[63] Continuation of Ser. No. 112,975, Oct. 23, 1987, abandoned.

[51] Int. Cl.$^4$ ................................................ A61K 7/09
[52] U.S. Cl. ............................................. 424/70; 424/78
[58] Field of Search .................... 524/837; 424/63, 78, 424/71, 70

[56] References Cited

U.S. PATENT DOCUMENTS

| | | |
|---|---|---|
| 3,325,439 | 6/1967 | Steinbach ........................ 260/32.8 |
| 3,681,122 | 8/1972 | Domicone et al. ................. 117/124 |
| 3,957,970 | 5/1976 | Korkis . |
| 3,964,500 | 6/1976 | Drakoff . |
| 4,185,087 | 1/1980 | Morlino . |
| 4,344,763 | 8/1982 | Tolgyesi et al. . |
| 4,364,837 | 12/1982 | Pader . |
| 4,387,090 | 6/1983 | Bolich . |
| 4,450,152 | 5/1984 | Ona et al. . |
| 4,487,883 | 12/1984 | Homan . |
| 4,502,889 | 3/1985 | Kurita . |
| 4,515,784 | 5/1985 | Bogardus et al. . |
| 4,529,586 | 7/1985 | DeMarco et al. . |
| 4,559,227 | 12/1985 | Chandra et al. ...................... 424/70 |

FOREIGN PATENT DOCUMENTS

| | | |
|---|---|---|
| 0155806A2 | 10/1985 | European Pat. Off. .............. 424/70 |
| 57-162-768-A | 10/1982 | Japan . |
| 61-044-972-A | 3/1986 | Japan . |
| 61-195-138-A | 8/1986 | Japan . |
| 2170216A | 7/1986 | United Kingdom . |

Primary Examiner—Joseph L. Schofer
Assistant Examiner—Jeffrey T. Smith
Attorney, Agent, or Firm—Douglas C. Mohl; Gretchen R. Hatfield; Steven J. Goldstein

[57] ABSTRACT

Hair care compositions which give both improved style retention and hair conditioning properties and easier processing. The compositions comprise from about 0.01% to about 10.0% of a filler reinforced silicone gum, from about 0.01% to about 10.0% of a silicone resin and a volatile carrier.

13 Claims, No Drawings

HAIR CARE COMPOSITIONS

This is a continuation of application Ser. No. 112,975, filed on Oct. 23, 1987 now abandoned.

TECHNICAL FIELD

The present invention relates to hair care compositions which have improved hair conditioning and style retention properties due to the inclusion of particular combination of silicone polymers, and a volatile carrier for such polymers.

BACKGROUND OF THE INVENTION

The desire to have hair retain a particular shape is widely held. The two methodologies of accomplishing this are permanent chemical alteration of the hair or a temporary alteration. A temporary alteration is one which can be removed by water or by shampooing. This has generally been accomplished by means of the application of a separate composition to dampened hair, i.e., after shampoong and/or conditioning, and prior to drying and/or styling. The materials used to provide setting benefits have generally been resins or gums and have been applied in the form of mousses, gels, lotions, and sprays. However, many people desire some improvement in style retention without the necessity of a separate step. Further, some people desire a high level of style retention such as that provided by a separate composition without the negative impact of these materials on dry hair properties, particularly ease of combing and hair feel.

Silicones in various hair care compositions have been disclosed in a large number of different publications, including U.S. Pat. No. 3,964,500, Drakoff, issued June 22, 1976; U.S. Pat. No. 4,364,837, Pader, issued Dec. 21, 1981; U.S. Pat. No. 4,341,799, Good, issued July 27, 1982; U.S. Pat. No. 4,465,619, Boskamp, issued Aug. 14, 1984; U.S. Pat. No. 4,515,784, Bogartus, issued May 7, 1985; U.S. Pat. No. 4,387,090, Bolich, issued June 7, 1983; and U.S. Pat. No. 4,529,586, DeMarco et al, issued July 16, 1985.

It has now been discovered that hair care compositions comprising a mixture of certain rigid silicone polymers in volatile carriers provide increased style retention. The compositions may be in any of the conventional forms, including but not limited to shampoos, conditioners, hairsprays, tonics, lotions and mousses. The compositions provide the increased style retention to the hair without decreasing dry hair properties such as ease of combing. A mixture of rigid silicones provides these benefit by depositing in a form that is the correct rigidity without tack. Specifically, combining of a filter reinforced silicone gum and a silicone resin provide these properties.

This is surprising since other silicone materials which have been typically used in hair care compositions as conditioners have hurt style retention, and the resins used frequently for style retention have generally hurt dry hair properties such as combing.

It is an object of the present invention to provide hair care compositions which contain a mixture of certain rigid silicone polymers and a volatile carrier.

It is a further object of the present invention to provide hair care compositions providing good style retention.

It is a further object of the present invention to provide hair care compositions which provide good conditioning.

These and other objects will become readily apparent from the detailed description which follows.

Unless otherwise indicated, all percentages and ratios herein are by weight.

SUMMARY OF THE INVENTION

The present invention relates to hair care compositions comprising from about 0.01% to about 10.0% of a filler reinforced silicone gum from about 0.01% to about 10.0% of a silicone resin and from about 0.1% to about 99.9% of a volatile carrier or mixtures thereof.

DETAILED DESCRIPTION OF THE INVENTION

The essential as well as optional components are described below.

RIGID SILICONE POLYMER MIXTURE

The compositions of the present invention contain a mixture of rigid silicone polymers which when applied to hair impart style retention benefits.

The rigid silicone polymer mixtures useful in the present invention have complex viscosities of at least $2 \times 10^5$ poise (p), preferably about $1 \times 10^7$ or more, where complex viscosity is measured by subjecting a sample to oscillatory shear at a fixed frequency of 0.1 rad/sec at 25° C. using a Rheometric Fluids Spectrometer ® measuring films having a thickness of about 1 millimeter. The resulting viscous and elastic modulii are combined to determine the complex modulus which is divided by the imposed frequency to compute the complex viscosity.

A preferred siloxane gum useful in the present invention is a dimethyl polysiloxane gum having a molecular weight of at least about 500,000. The siloxane gums are filler reinforced to provide additional rigidity. Silica is the preferred filler and is used at a level of from about 0.02% to about 20.0% by weight of the gum.

Silicone resins are silicone polymers with a high degree of crosslinking introduced through the use of trifunctional and tetrafunctional silanes. Typical silanes used in the manufacture of resins are monomethyl, dimethyl, monophenyl, diphenyl, methylphenyl, monovinyl, and methylvinyl chlorosilanes, together with tetrachlorosilane. A preferred resin is one offered by General Electric as GE SR545. This resin is provided as a solution in cyclomethicone.

As is noted above, the gum comprises from about 0.01% to about 10.0%, preferably from about 0.1% to about 2.0% of the total composition. Similarly the level of resin is from about 0.01% to about 10.0%, preferably from about 0.5% to about 5.0% of the total composition.

The filler reinforced silicone gum and the silicone resin are mixed under high shear in the presence of the volatile carrier.

VOLATILE CARRIER

The compositions of the invention comprise a volatile carrier, or mixtures thereof, for the silicone polymer. The level of carrier is generally from about 0.1% to about 99.9%. The term "volatile" as used herein means that the material has a measurable vapor pressure.

Where the siloxane gum is a polydimethyl siloxane or a polydiphenyldimethyl siloxane, the preferred carriers are volatile silicones having a boiling point between 99° C. to about 260° C. and having a solubility in water of less than about 0.1% at 25° C. The degree of substitution on the siloxane polymer (higher substitution), lower solubility) obviously affects the polymer's solubility and is taken into account by the formulator. The silicone carriers may be either cyclic or linear polydimethyl siloxanes. The number of silicon atoms in the cyclic silicones is about 3 to about 7, most preferably 4 or 5. The general formula for the cyclic silicones is:

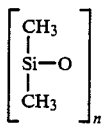

wherein $n=3-7$. Viscosities are generally less than 10 centipoise (cp) at 25° C.

Linear polydimethyl siloxane carriers useful in the invention generally have viscosities of less than about 5 cP at 25° C. The linear volatile silicones contain from about 3 to about 9 silicone atoms and have the general formula

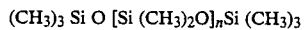

wherein $n=1-7$.

Silicones of the above described types are widely available e.g., from Dow Corning as 344,345 and 200 fluids; Union Carbide as Silicone 7202 and 7158, and Stauffer Chemical as SWS-03314.

Also useful in compositions of the invention are certain volatile hydrocarbons. These hydrocarbons may be either straight chain or branched, and contain from about 10 to about 16 carbon atoms, preferably from about 12 to about 16 carbon atoms.

Water is also useful in compositions of the present invention either alone or in mixtures with other volatile carriers.

Short chain alcohols such as ethanol are also suitable solvents for use in the present compositions.

OPTIONAL INGREDIENTS

Surfactants

Surfactants are preferred optional ingredients in the compositions of the invention, particularly shampoo and conditioner compositions. When present, the surfactant comprises from about 0.05% to about 50% of the total composition. For a shampoo, the level is preferably from about 10% to about 30%, most preferably from about 12% to about 25% of the composition. For conditioners the preferred level of surfactant is from about 0.2% to about 3%. Surfactants useful in compositions of the invention include anionic, nonionic, cationic, zwitterionic and amphoteric surfactants.

Synthetic anionic detergents useful herein, particularly for the shampoo compositions, include alkyl and alkyl ether sulfates. These materials have the respective formulae $ROSO_3M$ and $RO(C_2H_4O)_xSO_3M$ wherein R is alkyl or alkenyl of about 10 to about 20 carbon atoms, x is 1 to 10, and M is a water-soluble cation such as ammonium, sodium, potassium and triethanolamine. The alkyl ether sulfates useful in the present invention are condensation products of ethylene oxide and monohydric alcohols having about 10 to about 20 carbon atoms. Preferably, R has 12 to 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with 1 to 10, and especially 3, molar proportions of ethylene oxide and the resulting mixture of molecular species, having, for example, an average of 3 moles of ethylene oxide per mole of alcohol, is sulfated and neutralized.

Specific examples of alkyl ether sulfates of the present invention are sodium coconut alkyl triethylene glycol ether sulfate; lithium tallow alkyl triethylene glycol ether sulfate; and sodium tallow alkyl hexaoxyethylene sulfate. Highly preferred alkyl ether sulfates are those comprising a mixture of individual compounds, said mixture having an average alkyl chain length of from about 12 to 16 carbon atoms and an average degree of ethoxylation of from about 1 to 4 moles of ethylene oxide. Such a mixture also comprises from about 0 to 20% by weight $C_{12-13}$ compounds, from 60 to 100% by weight of $C_{14-15-16}$ compounds, from about 0 to 20% by weight of $C_{17-18-19}$ compounds; from about 3 to 30% by weight of compounds having a degree of ethoxylation of 0; from about 45 to 90% by weight of compounds having a degree of ethoxylation of from 1 to 4; from about 10 to 25% by weight of compounds having a degree of ethoxylation of from 4 to 8; and from about 0.1 to 15% by weight of compounds having a degree of ethoxylation greater than 8.

Another suitable class of anionic surfactants are the water-soluble salts of the organic, sulfuric acid reaction products of the general formula:

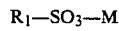

wherein $R_1$ is chosen from the group consisting of a straight or branched chain, saturated aliphatic hydrocarbon radical having from 8 to 24, preferably 12 to 18, carbon atoms; and M is a cation. Important examples are the salts of an organic sulfuric acid reaction product of a hydrocarbon of the methane series, including iso-, neo-, ineso-, and n-paraffins, having 8 to 24 carbon atoms, preferably 12 to 18 carbon atoms and a sulfonating agent e.g., $SO_3$, $H_2SO_4$, oleum, obtained according to known sulfonation methods, including bleaching and hydrolysis. Preferred are alkali metal and ammonium sulfonated $C_{12-18}$- n-paraffins.

Additional examples of anionic synthetic detergents which come within the terms of the present invention are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, or example, are derived from coconut oil. Other anionic synthetic detergents of this variety are set forth in U.S. Pat. Nos. 2,486,921; 2,486,922; and 2,396,278.

Still other anionic synthetic detergents include the class designated as succinamates. This class includes such surface active agents as disodium N-octadecylsulfosuccinamate; tetrasodium N-(1,2-dicarboxyethyl)-N-octadecylsulfo-succinamate; diamyl ester of sodium sulfosuccinic acid; dihexyl ester of sodium sulfosuccinic acid; dioctyl esters of sodium sulfosuccinic acid.

Other suitable anionic detergents utilizable herein are olefin sulfonates having about 12 to about 24 carbon atoms. The term "olefin sulfonates" is used herein to mean compounds which can be produced by the sulfonation of α-olefins by means of uncomplexed sulfur trioxide, followed by neutralization of the acid reaction mixture in conditions such that any sultones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The α-olefins from which the olefin sulfonates are derived are mono-olefins having 12 to 24 carbon atoms, preferably 14 to 16 carbon atoms. Preferably, they are straight chain olefins. Examples of suitable 1-olefins include 1-dodecene; 1-tetradecene; 1-hexadecene; 1-octadecene; 1-eicosene and 1-tetracosene.

In addition to the true alkene sulfonates and a proportion of hydroxy-alkanesulfonates, the olefins sulfonates can contain minor amounts of other materials, such as alkene disulfonates depending upon the reaction conditions, proportion of reactants, the nature of the starting olefins and impurities in the olefin stock and side reactions during the sulfonation process.

The α-olefins from which the olefin sulfonates are derived are mono-olefins having 12 to 24 carbon atoms, preferably 14 to 16 carbon atoms. Preferably, they are straight chain olefins. Examples of suitable 1-olefins include 1-dodecene; 1-tetradecene; 1-hexadecene; 1-octadecene; 1-eicosene and 1-tetracosene.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific α-olefin sulfonate mixture of the above type is described more fully in the U.S. Pat. No. 3,332,880 of Phillip F. Pflaumer and Adrian Kessler, issued July 25, 1967, titled "Detergent Composition", the disclosure of which is incorporated herein by reference.

Another class of anionic organic detergents are the β-alkyloxy alkane sulfonates. These compounds have the following formula:

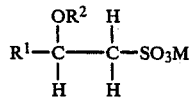

wherein $R^1$ is a straight chain alkyl group having from 6 to 20 carbon atoms, $R^2$ is a lower alkyl group having from 1 (preferred) to 3 carbon atoms, and M is a water-soluble cation as hereinbefore described.

Specific examples of β-alkyloxy-alkane-1-sulfonates, or alternatively 2-alkyloxy-alkane-1-sulfonates, having low hardness (calcium ion) sensitivity useful herein to provide superior cleaning levels under household washing conditions include:

potassium-β-methoxydecanesulfonate, sodium 2-methoxytridecanesulfonate, potassium 2-ethoxytetradecylsulfonate, sodium 2-isopropoxyhexadecylsulfonate, lithium 2-t-butoxytetradecylsulfonate, sodium β-methoxyoctadecylsulfonate, and ammonium β-n-propoxydodecylsulfonate.

Nonionic surfactants, which are preferably used in combination with an anionic, amphoteric or zwitterionic surfactant, can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

4. Long chain tertiary amine oxides corresponding to the following general formula:

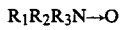

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyldi(2-hydroxyethyl) amine oxide, dimethyloctylamine oxide, dimethyl-decylamine oxide, dimethyltetradecylamine oxide, 3,6,9-trioxaheptadecyldiethylamine oxide, di(2-hydroxyethyl)-tetradecylamine oxide, 2-dode-coxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

wherein R contains an alkyl, alkenyl or monohydroxyalkyl radical ranging from 8 to 18 carbon atoms in chain length, from 0 to about 10 ethylene oxide moieties and from 0 to 1 glyceryl moiety and R' and R" are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecyldimethylphosphine oxide, tetradecylmethylethylphosphine oxide, 3,6,9-trioxaoctadecyldimethylphosphine oxide, cetyldimethylphosphine oxide, 3-dodecoxy-2-hydroxypropyldi(2-hydroxyethyl) phosphine oxide, stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oleyldimethylphosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

Cationic surfactants useful in compositions of the present invention, particularly the conditioner composition, contain amino or quaternary ammonium hydrophilic moieties which are positively charged when dissolved in the aqueous composition of the present invention. Cationic surfactant vehicle materials among those useful herein are disclosed in the following documents, all incorporated by reference herein: M. C. Publishing Co., *McCutcheon's, Detergents & Emulsifiers*, (North American edition 1979); Schwartz, et. a., *Surface Active Agents, Their Chemistry and Technology*, New York: Interscience Publishers, 1949; U.S. Pat. No. 3,155,591, Hilfer, issued Nov. 3, 1964; U.S. Pat. No. 3,929,678, Laughlin, et al., issued Dec. 30, 1975; U.S. Pat. No. 3,959,461, Bailey, et al., issued May 25, 1976; and U.S. Pat. No. 4,387,090, Bolich Jr., issued June 7, 1983.

Among the quaternary ammonium-containing cationic surfactant materials useful herein are those of the general formula:

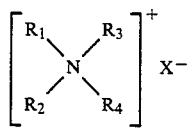

wherein $R_1$ is hydrogen, an aliphatic group of from 1 to 22 carbon atoms, or an aromatic, aryl or alkylaryl group having from 12 to 22 carbon atoms; $R_2$ is an aliphatic group having from 1 to 22 carbon atoms; $R_3$ and $R_4$ are each alkyl groups having from 1 to 3 carbon atoms, and X is an anion selected from halogen, acetate, phosphate, nitrate and alkylsulfate radicals. The aliphatic groups may contain, in addition to carbon and hydrogen atoms, ether linkages, and other groups such as amido groups.

Other quaternary ammonium salts useful herein are of the formula:

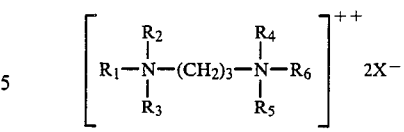

wherein $R_1$ is an aliphatic group having from 16 to 22 carbon atoms, $R_2$, $R_3$, $R_4$, $R_5$ and $R_6$ are selected from hydrogen and alkyl having from 1 to 4 carbon atoms, and X is an ion selected from halogen, acetate, phosphate, nitrate and alkyl sulfate radicals. Such quaternary ammonium salts include tallow propane diammonium dichloride.

Preferred quaternary ammonium salts include dialkyldimethylammonium chlorides, wherein in the alkyl groups have from 12 to 22 carbon atoms and are derived from long-chain fatty acids, such as hydrogenated tallow fatty acid. (Tallow fatty acids give rise to quaternary compounds wherein $R_1$ and $R_2$ have predominately from 16 to 18 carbon atoms). Examples of quaternary ammonium salts useful in the present invention include ditallow-dimethyl ammonium chloride, ditallowdimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl) dimethyl ammonium chloride, and stearyl dimethyl benzyl ammonium chloride. Ditallow dimethyl ammonium chloride, dicetyl dimethyl ammonium chloride, stearyl dimethyl benzyl ammonium chloride and cetyl trimethyl ammonium chloride are preferred quaternary ammonium salts useful herein. Di-(hydrogenated tallow) dimethyl ammonium chloride is a particularly preferred quaternary ammonium salt.

Salts of primary, secondary and tertiary fatty amines are also preferred cationic surfactant vehicle materials. The alkyl groups of such amines preferably have from 12 to 22 carbon atoms, and may be substituted or unsubstituted. Secondary and tertiary amines are preferred, tertiary amines are particularly preferred. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearylamine formate and N-tallowpropane diamine dichloride and stearamidopropyl dimethylamine citrate. Cationic amine surfactants included among those useful in the present invention are disclosed in U.S. Pat. No. 4,275,055, Nachtigal, et al., issued June 23, 1981 (incorporated by reference herein).

Zwitterionic surfactants, useful in shampoos as well as conditioners, can be exemplified by those which can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

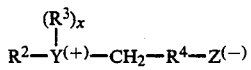

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphonate, and phosphate groups.

Examples include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatetradexocylphosphonio]-2-hydroxypropane-1-phosphate;
3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl)ammonio]-butane-1-carboxylate;
3-[S-ethyl-S-(3-dodecoxy-2-hydroxypropyl)sulfonio]-propane-1-phosphate;
3-[P,P-dimethyl-P-dodecylphosphonio]-propane-1-phosphonate; and
5-[N,N-di(3-hydroxypropyl)-N-hexadecylammonio]-2-hydroxypentane-1-sulfate.

Other zwitterionics such as betaines are also useful in the present invention. Examples of betaines useful herein include the high alkyl betaines such as coco dimethyl carboxymethyl betaine, lauryl dimethyl carboxymethyl betaine, lauryl dimethyl alpha-carboxyethyl betaine, cetyl dimethyl carboxymethyl betaine, lauryl bis-(2-hydroxy-ethyl) carboxy methyl betaine, stearyl bis-(2-hydroxy-propyl) carboxymethyl betaine, oleyl dimethyl gamma-carboxypropyl betaine, lauryl bis-(2-hydroxypropyl) alpha-carboxyethyl betaine, etc. The sulfobetaines may be represented by coco dimethyl sulfopropyl betaine, stearyl dimethyl sulfopropyl betaine, lauryl dimethyl sulfoethyl betaine, lauryl bis-(2-hydroxy-ethyl) sulfopropyl betaine and the like; amido betaines and amidosulfobetaines, wherein the RCONH(CH$_2$)$_3$ radical is attached to the nitrogen atom of the betaine are also useful in this invention. The amido betaines are preferred for use in some of the compositions of this invention.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

Other Optional Components

Where the hair care compositions are conditioner compositions, preferred optional components include gel vehicle materials. The vehicle comprises two essential components: a lipid vehicle material and a cationic surfactant vehicle material. Such gel-type vehicles are generally described in the following documents, all incorporated by reference herein: Barry, "The Self Bodying Action of the Mixed Emulsifier Sodium Dodecyl Sulfate/Cetyl Alcohol", 28 *J. of Colloid and Interface Science* 82–91 (1968); Barry, et al., "The Self-Bodying Action of Alkyltrimethylammonium Bromides/Cetostearyl Alcohol Mixed Emulsifiers; Influence of Quaternary Chain Length", 35 *J. of Colloid and Interface Science* 689–708 (1971); and Barry et al., "Rheology of Systems Containing Cetomacrogol 1000—Cetostearyl Alcohol, I. Self Bodying Action", 38 *J. of Colloid and Interface Science* 616–625 (1972).

Lipid vehicle materials include naturally or synthetically-derived acids, acid derivatives, alcohols, esters, ethers, ketones, and amides with carbon chains of from 12 to 22, preferably from 16 to 18, carbon atoms in length. Fatty alcohols and fatty esters are preferred; fatty alcohols are particularly preferred.

Lipid vehicle materials among those useful herein are disclosed in *Bailey's Industrial Oil and Fat Products*, (3d edition, D. Swern, ed. 1979) (incorporated by reference herein). Fatty alcohols included among those useful herein are disclosed in the following documents, all incorporated by reference herein: U.S. Pat. No. 3,155,591, Hilfer, issued Nov. 3, 1964; U.S. Pat. No. 4,165,369, Watanabe, et al., issued Aug. 21, 1979; U.S. Pat. No. 4,269,824, Villamarin, et al., issued May 26, 1981; British Specification 1,532,585, published Nov. 15, 1978; and Fukushima, et al., "The Effect of Cetostearyl Alcohol in Cosmetic Emulsions", 98 *Cosmetics & Toiletries* 89–102 (1983). Fatty esters included among those useful herein are disclosed in U.S. Pat. No. 3,341,465, Kaufman, et al., issued Sept. 12, 1967 (incorporated by reference herein.)

Preferred esters for use herein include cetyl palmitate and glycerylmonostearate. Cetyl alcohol and stearyl alcohol are preferred alcohols. A particularly preferred lipid vehicle material is comprised of a mixture of cetyl alcohol and stearyl alcohol containing from about 55% to about 65% (by weight of mixture) of cetyl alcohol.

Other vehicles, suitable for use with the rigid silicones herein are, for example, tonics, mousses, pump sprays and hairsprays. Tonics and pump sprays utilize a solvent such as water or alcohol while mousses and hairsprays additionally utilize a propellant such trichlorofluoromethane, dichlorodifluoromethane, dimethylether, propane, n-butane or isobutane in addition to the rigid silicone and optional components as set forth below. The level of propellant can be adjusted as desired but is generally from about 3% to about 30% for mousses and from about 15% to about 40% for hairsprays.

The hair care compositions herein can also contain a variety of other optional components suitable for rendering such compositions more acceptable. Such conventional optional ingredients are well known to those skilled in the art, e.g., pearlescent aids such as ethylene glycol distearate; preservatives such as benzyl alcohol, methyl paraben, propyl paraben and imidazolidinyl urea; thickeners and viscosity modifiers such as a diethanolamide of a long chain fatty acid (e.g., PEG 3 lauric diethanolamide), cocmonoethanol amide, dimethicone copolyols, guar gum, methyl cellulose starches and starch derivatives, fatty alcohols such as cetearyl alcohol, sodium chloride, sodium sulfate, polyvinyl alcohol, and ethyl alcohol; pH adjusting agents such as citric acid, sodium citrate, succinic acid, phosphoric acid, sodium hydroxide, sodium carbonate, etc.; coloring agents such as any of the FD&C or D&C dyes; hair oxidizing (bleaching) agents such as hydrogen peroxide, perborate and persulfate salts, hair reducing agents such as the thioglycolates; perfumes; and, sequestering agents such as disodium ethylenediamine tetraacetate, polymer plasticizing agents such as glycerin and propylene glycol. Such agents generally are used individually at a level of from about 0.01% to about 10%, preferably from about 0.05% to about 5.0% by weight of the composition.

The pH of the present compositions is not critical and may be in the range of from about 3 to about 10.

As with all compositions, the present compositions should not contain components which unduly interfere with the performance of the compositions.

METHOD OF MANUFACTURE

Methods of manufacture of various types of hair care compositions are described in the following examples.

INDUSTRIAL APPLICABILITY

The present compositions are used in a conventional manner varying with the type of composition described.

DESCRIPTION OF PROCESS

The silicones are processed in the following manner. The filler reinforced silicone gum is blended under high shear with the silicone resin in the presence of a volatile carrier such as cyclomethicone. The blend is mixed until the filler reinforced silicone gum and the silicon resin are dispersed or dissolved in the volatile carrier. This silicone blend can then be added to various hair care compositions.

EXAMPLE I

Shampoo Examples

| Component | Weight % I | Weight % II |
|---|---|---|
| Ammonium Lauryl Sulfate | 13.5 | 13.5 |
| Ammonium Laureth Sulfate | 4.0 | 4.0 |
| Ammonium Xylene Sulfonate | 0.1 | 0.0 |
| Dimethicone Gum[1,4] | 0.52 | 1.32 |
| Silica[2,4] | 0.12 | 0.33 |
| Silicone Resin[3,4] | 1.30 | 3.30 |
| Cyclomethicone[4] | 0.67 | 1.71 |
| Perfume | 1.20 | 1.20 |
| Preservative | 0.033 | 0.033 |
| Cocoamide MEA | 4.0 | 4.0 |
| Ethylene Glycol Distearate | 2.0 | 2.0 |
| Cetearyl Alcohol | 0.60 | 1.00 |
| Sodium Citrate | 0.05 | 0.05 |
| Citric Acid | 0.05 | 0.05 |
| Sodium Hydroxide | 0.01 | 0.01 |
| Sodium Chloride | 1.0 | 1.0 |
| Water | Q.S. | Q.S |

[1] Dimethicone Gum - SE-30 gum supplied by General Electric Company
[2] Cab-O-Sil HS-5 supplied by Cabot Corporation
[3] Silicone Resin 176-11495 supplied by General Electric Company
[4] These components are combined in a silicone premix

Shampoo Processing

Ammonium lauryl sulfate, citric acid, sodium citrate and sodium hydroxide are added to the distilled water at about 15° C. The mixture is heated to from 70° C. to 80° C. The cocamide MEA and glycol distearate are added at this point. The ammonium laureth-3 sulfate, cetearyl alcohol and silicone premix are blended at 70° C. to 90° C. This mixture is added to the batch following the glycol distearate. The preservative and fragrance are then added. The batch is mixed for 5 minutes, then milled under high shear using conventional milling apparatus and then cooled to room temperature (15° C. to 25° C.). Sodium chloride and ammonium xylene sulfonate are added for viscosity control as needed.

EXAMPLE II

Conditioner Examples

| Component | Weight % I | Weight % II |
|---|---|---|
| Cyclomethicone[1] | 4.41 | 3.90 |
| Cetyl Alcohol | 1.0 | 1.0 |
| Quaternium 18 | 0.85 | 0.85 |
| Silicone Resin[1] | 0.52 | 1.04 |
| Stearyl Alcohol | 0.75 | 0.75 |
| Hydroxyethyl Cellulose | 0.50 | 0.50 |
| Stearimidopropyl Dimethylamine | 0.50 | 0.50 |
| Ceteareth-20 | 0.35 | 0.35 |
| Glyceral Monostearate | 0.25 | 0.25 |
| Fragrance | 0.25 | 0.25 |
| Dimethicone Gum[1] | 0.208 | 0.208 |
| Citric Acid | 0.13 | 0.13 |
| Dimethicone Copolyol | 0.10 | 0.10 |
| Silica[1] | 0.052 | 0.052 |
| Preservative | 0.033 | 0.033 |
| Water | Q.S. | Q.S |

[1] These components are combined as a premix as in Example I.

Conditioner Processing

Hydroxyethyl cellulose is added to the distilled water at a temperature of 15° C. to 40° C. This mixture is well dispersed, then heated to a temperature of from 60° C. to 90° C. Materials 2 through 8 are added to the batch while the temperature is maintained in this range. The mixture is stirred for approximately 10 minutes, then cooled to approximately 50° C. The remaining materials are added at this temperature. The mixture is milled under high shear for approximately 2 minutes using a conventional milling apparatus, then cooled to room temperature.

EXAMPLE III

Hair Tonic Example

| Component | Weight % |
|---|---|
| Premix A | |
| Silicone Resin | 0.38 |
| Dimethicone Gum | 0.14 |
| Cyclomethicone | 0.95 |
| Silica | 0.04 |
| Cyclomethicone | 4.00 |
| Ethanol (SDA 40) | 40.00 |
| Fragrance | 0.10 |
| Triethanolamine | 0.10 |
| Dimethicone Copolyol | 0.167 |
| Carbomer 940 | 0.108 |
| Water | Q.S. |

The silicone blend (Premix A) and the dimethicone copolyol are milled under high shear with a conventional milling apparatus. This is added to the ethanol. The additional cyclomethicone is added next to the ethanol. The Carbomer 940 is mixed with the water until completely dispersed and then this premix is added to the ethanol mixture. The perfume is added and the complete mixture is milled for at least 10 minutes with a conventional milling apparatus. The triethanolamine is mixed in to neutralize the Carbomer 940 and thicken the mixture.

What is claimed is:

1. A hair care composition comprising:
   (a) from about 0.01% to about 10.0% of a silica reinforced silicone gum;
   (b) from about 0.01% to about 10.0% of a silicone resin; and
   (c) a volatile carrier.

2. A hair care composition according to claim 1 wherein the rigid silicone gum is filler reinforced polydimethyl siloxane gum.

3. A hair care composition according to claim 2 wherein the volatile carrier is a cyclic silicone containing from about 3 to about 7 silicon atoms.

4. A hair care composition according to claim 3 in the form of a shampoo which in addition contains from about 10% to about 35% of a synthetic surfactant or mixtures thereof.

5. A hair care composition according to claim 4 wherein the synthetic surfactant is selected from the group consisting of alkyl sulfates, ethoxylated alkyl sulfates and mixtures thereof.

6. A hair care composition according to claim 5 wherein the filler reinforced silicone gum is present at a level of from about 0.1% to about 2.0% and the silicone resin is present at a level of from about 0.5% to about 5%.

7. A hair care composition according to claim 3 in the form of a conditioner which additionally contains from about 0.1% to about 10.0% of a lipid vehicle material and from about 0.05% to about 5.0% of a cationic surfactant.

8. A hair care composition according to claim 7 wherein the cationic surfactant is a quaternary ammonium salt.

9. A hair care composition according to claim 8 wherein the lipid vehicle material is selected from the group consisting of cetyl alcohol, stearyl alcohol, cetyl palmitate, glyceryl monostearate and mixtures thereof.

10. A hair care composition according to claim 1 in the form of hair tonic.

11. A hair care composition according to claim 1 in the form of hairspray or pump spray.

12. A hair care composition according to claim 1 in the form of a mousse.

13. A method of conditioning hair comprising treating the hair with a composition according to claim 4.

* * * * *